US008318078B2

(12) United States Patent
Jagger et al.

(10) Patent No.: US 8,318,078 B2
(45) Date of Patent: Nov. 27, 2012

(54) ASYMMETRIC STENT DELIVERY SYSTEM WITH PROXIMAL EDGE PROTECTION AND METHOD OF MANUFACTURE THEREOF

(75) Inventors: Karl A. Jagger, Deephaven, MN (US); Linda S. Christenson, Corcoran, MN (US); Todd Rowe, Excelsior, MN (US); Stanley Nordin, Monticello, MN (US); Daniel Nygaard, New Brighton, MN (US); Randall J. Beyreis, Corcoran, MN (US); Jon Livingston, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2265 days.

(21) Appl. No.: 10/601,952

(22) Filed: Jun. 23, 2003

(65) Prior Publication Data

US 2004/0260379 A1    Dec. 23, 2004

(51) Int. Cl.
*A61F 2/84* (2006.01)
(52) U.S. Cl. .......................... 264/523; 29/282; 623/1.11
(58) Field of Classification Search .................. 606/191, 606/192, 194, 200; 604/96.01; 128/887, 128/897–899; 623/1.11, 1.23, 1.1, 1.13–1.15; 29/283.5, 282, 283.2, 508, 515, 516; 264/523
See application file for complete search history.

(56) References Cited

U.S. PATENT DOCUMENTS

| 3,868,956 A | 3/1975 | Alfidi et al. |
| 4,733,665 A | 3/1988 | Palmaz |
| 4,768,507 A | 9/1988 | Fischell et al. |
| 5,041,093 A | 8/1991 | Chu |
| 5,071,407 A | 12/1991 | Termin et al. |

(Continued)

FOREIGN PATENT DOCUMENTS

WO    WO 02066095 A2 *   8/2002

OTHER PUBLICATIONS

International Preliminary Report on Patentability dated Jan. 12, 2006.

*Primary Examiner* — Kathleen Sonnett
(74) *Attorney, Agent, or Firm* — Seager, Tufte & Wickhem LLC (57) ABSTRACT

A balloon catheter stent deployment system is disclosed wherein a balloon catheter is provided and a tubular stent is crimped onto a distal portion of the balloon with a distal end of the stent in close proximity to a point where the distal end of the balloon is attached to the inner tube of the catheter. A proximal section of the balloon extending from a proximal end of the stent to a point where the proximal end of the balloon is attached to the outer shaft of the catheter remains uncovered by the stent and, has a larger uninflated outer diameter than the crimped stent. Thus, in some embodiments, the proximal section of the balloon provides a protective cone for the proximal end of the stent to help resist frictional forces from disengaging the stent from the balloon in the event the balloon catheter and stent are withdrawn back into a guide catheter during a procedure. A stepped enclosure is also disclosed which is used in a disclosed fabrication method to allow the proximal section of the balloon to be inflated after the stent is crimped onto the distal section of the balloon.

12 Claims, 4 Drawing Sheets

U.S. PATENT DOCUMENTS

| | | | |
|---|---|---|---|
| 5,074,845 A * | 12/1991 | Miraki et al. | 604/103.08 |
| 5,108,416 A | 4/1992 | Ryan et al. | |
| 5,147,302 A * | 9/1992 | Euteneuer et al. | 604/103 |
| 5,201,757 A | 4/1993 | Heyn et al. | |
| 5,409,495 A | 4/1995 | Osborn | |
| 5,445,646 A | 8/1995 | Euteneuer et al. | |
| 5,476,505 A | 12/1995 | Limon | |
| 5,534,007 A | 7/1996 | St. Germain et al. | |
| 5,571,135 A | 11/1996 | Fraser et al. | |
| 5,571,168 A | 11/1996 | Toro | |
| 5,591,172 A | 1/1997 | Bachmann et al. | |
| 5,634,928 A | 6/1997 | Fischell et al. | |
| 5,662,703 A | 9/1997 | Yurek et al. | |
| 5,683,451 A | 11/1997 | Lenker et al. | |
| 5,702,418 A | 12/1997 | Ravenscroft | |
| 5,709,703 A | 1/1998 | Lukic et al. | |
| 5,735,859 A | 4/1998 | Fischell et al. | |
| 5,772,669 A | 6/1998 | Vrba | |
| 5,776,142 A | 7/1998 | Gunderson | |
| 5,782,855 A | 7/1998 | Lau et al. | |
| 5,810,871 A | 9/1998 | Tuckey et al. | |
| 5,817,102 A | 10/1998 | Johnson et al. | |
| 5,836,965 A * | 11/1998 | Jendersee et al. | 623/1.11 |
| 5,843,092 A | 12/1998 | Heller et al. | |
| 5,893,868 A * | 4/1999 | Hanson et al. | 623/1.11 |
| 5,908,448 A | 6/1999 | Roberts et al. | |
| 5,920,975 A * | 7/1999 | Morales | 29/282 |
| 5,944,726 A | 8/1999 | Blaeser et al. | |
| 6,019,778 A | 2/2000 | Wilson et al. | |
| 6,056,906 A | 5/2000 | Werneth et al. | |
| 6,077,295 A | 6/2000 | Limon et al. | |
| 6,106,530 A | 8/2000 | Harada | |
| 6,168,617 B1 | 1/2001 | Blaeser et al. | |
| 6,174,316 B1 | 1/2001 | Tuckey et al. | |
| 6,264,683 B1 | 7/2001 | Stack et al. | |
| 6,302,893 B1 | 10/2001 | Limon et al. | |
| 6,391,032 B2 | 5/2002 | Blaeser et al. | |
| 6,416,529 B1 | 7/2002 | Holman et al. | |
| 6,423,089 B1 | 7/2002 | Gingras et al. | |
| 6,432,129 B2 | 8/2002 | DiCaprio | |
| 6,432,130 B1 | 8/2002 | Hanson | |
| 6,447,521 B1 | 9/2002 | Mouw et al. | |
| 6,464,718 B1 | 10/2002 | Miller et al. | |
| 6,468,299 B2 | 10/2002 | Stack et al. | |
| 6,478,814 B2 | 11/2002 | Wang et al. | |
| 6,520,983 B1 | 2/2003 | Colgan et al. | |
| 6,527,739 B1 | 3/2003 | Bigus et al. | |
| 6,533,806 B1 | 3/2003 | Sullivan et al. | |
| 6,533,807 B2 | 3/2003 | Wolinsky et al. | |
| 6,544,268 B1 | 4/2003 | Lazarus | |
| 6,547,813 B2 | 4/2003 | Stiger et al. | |
| 6,561,788 B1 * | 5/2003 | Gaudoin | 425/522 |
| 6,562,064 B1 | 5/2003 | deBeer | |
| 6,572,643 B1 | 6/2003 | Gharibadeh | |
| 6,576,006 B2 | 6/2003 | Limon et al. | |
| 6,629,350 B2 * | 10/2003 | Motsenbocker | 29/283.5 |
| 6,948,223 B2 * | 9/2005 | Shortt | 29/272 |
| 6,986,742 B2 | 1/2006 | Hart et al. | |
| 2003/0032999 A1 | 2/2003 | Huang | |
| 2003/0208254 A1 | 11/2003 | Shortt | |
| 2003/0208255 A1 | 11/2003 | O'Shaughnessy et al. | |
| 2003/0236563 A1 | 12/2003 | Fifer | |

* cited by examiner

ASYMMETRIC STENT DELIVERY SYSTEM WITH PROXIMAL EDGE PROTECTION AND METHOD OF MANUFACTURE THEREOF

TECHNICAL FIELD

A balloon catheter stent deployment system is disclosed which has an asymmetric longitudinal profile. In some embodiments, the configuration of the balloon allows for protection of the proximal edge of the stent in the event the stent and balloon must be withdrawn or retracted. Such a configuration can provide centering characteristics for the device. A method of manufacture of the disclosed balloon catheter stent deployment system is also disclosed as well as a tool used in the manufacture of the disclosed system.

DESCRIPTION OF THE RELATED ART

Intravascular catheters are widely used for a variety of diagnostic and therapeutic purposes. Specifically, angioplasty has been developed as an alternative to bypass surgery for treating vascular diseases or other conditions that occlude or reduce blood flow in a patient's vascular system. Balloon angioplasty has proven to be a useful and often a preferred treatment for coronary diseases that cause blockages, also known as stenoses, in coronary arteries as well as other parts of the vascular system. In balloon angioplasty, intravascular devices known as balloon catheters are utilized.

Most balloon catheters have a relatively long and flexible tubular shaft defining one or more passages or lumens, and an inflatable balloon attached near one end of the shaft. This end of the catheter where the balloon is located will herein be referred to as the "distal" end, while the other end will herein be referred to as the "proximal" end. The balloon is connected to one of the lumens extending through the shaft for the purpose of selectively inflating and deflating the balloon. The other end of this inflation lumen leads to a hub coupling at the other end for connecting the shaft lumens to various equipment used to inflate the balloon.

In practice, a guidewire is inserted into the patient's vascular system through a guide catheter. The balloon catheter assembly is then fed through the guide catheter and over the guidewire. The balloon catheter is loaded onto the guidewire by inserting the proximal end of the guidewire into the distal end of the catheter. While maintaining the position of the guidewire within the vascular system, the catheter is advanced along the length of the guidewire. The proximal end of the guidewire may exit through a proximal guide wire port in the catheter.

After the balloon is located at the desired site, it is inflated to press radially outward on the blood vessel wall at relatively high pressure to a relatively constant diameter. This outward pressing on the stenosis or narrowing at the desired site in the vessel is intended to partially or completely re-open or dilate vessel, increasing its inner diameter or cross-sectional area through which blood flows, resulting in greater blood flow through the newly expanded vessel.

While angioplasty is effective in alleviating arterial stenosis in an artery or vessel, in many cases, the vessel may restenose or close down, thereby negating the positive affect of the angioplasty procedure, and possibly requiring an additional angioplasty procedure. To reduce the risk of restenosis, various stent devices have been used for mechanically keeping the affected vessel area open after completion of the angioplasty procedure.

Some stents are expanded to the proper size by inflating a balloon catheter, and are commonly referred to as "balloon-expandable" stents, while others are designed to elastically resist compression in a "self-expanding" manner. Both balloon-expandable stents and self-expanding stents are generally crimped or compressed to a diameter during delivery that is smaller than the eventual deployed diameter at the desired site. When positioned at the desired site within the lesion, they are deployed by inflating a balloon or being allowed to self-expand into the desired diameter.

Frictional forces generated as the catheter assembly is moved through a vasculature system may tend to cause the crimped stent to slip on the balloon in a proximal direction while the catheter system is advanced, or to slip in a distal direction if the physician decides to withdraw the stent without deploying the stent. The frictional forces can increase if the stent and balloon are not centered within the vessel or guide catheter as the catheter assembly is advanced or withdrawn. It is of course important to retain the stent in the proper position, during advancement or withdrawal along a vascular path.

Accordingly, as angioplasty and stent delivery procedures continue to increase, there is a need to provide improved stent delivery systems with improved stent retention on the balloon during advancement in and withdrawal from a vasculature system and also which provides improved centering of the entire device within a vessel during advancement withdrawal and deployment of the stent.

SUMMARY OF THE DISCLOSURE

In satisfaction of the afore-noted needs, a balloon catheter stent deployment system is disclosed which comprises a unique balloon configuration for carrying a balloon expandable stent. The balloon catheter comprises an inner-tubular shaft disposed within an outer-tubular shaft. The inner and outer shafts each have proximal and distal ends. The distal end of the inner shaft extends distally beyond the distal end of the outer shaft. The balloon catheter also comprises an inflatable balloon having a proximal end attached to the outer shaft near or at the distal end thereof and the balloon further has a distal end attached at or near the distal end thereof.

An expandable tubular stent can be mounted around a middle portion of the balloon. Specifically, the stent has a distal end disposed proximally to the distal end of the balloon and a proximal end spaced distally from the proximal end of the balloon. The stent is crimped onto the balloon so that the stent has an initial maximum outer diameter when the balloon is in an uninflated state.

The stent is typically shorter than the balloon which results in the balloon further having a proximal section that extends from the proximal end of the stent back to the point where the balloon is attached to the outer shaft. This proximal section of the balloon has an uninflated initial outer diameter greater than the initial outer diameter of the stent. This larger diameter of the proximal section of the balloon can protect the distal end of the stent from frictional forces in the event the balloon catheter needs to be withdrawn during a procedure. This larger diameter of the proximal section of the balloon can also provide a centering action for the balloon and stent as the balloon catheter is advanced or withdrawn during a procedure.

The balloon further comprises a distal section extending from a distal end of the stent to a point where the balloon is attached to the inner shaft. The distal section of the balloon has an uninflated maximum outer diameter less than or equal to the initial maximum outer diameter of the stent resulting in improved trackability of the device.

A method for fabricating a balloon catheter stent deployment system is also disclosed. The disclosed method includes providing a balloon as described above, placing a stent over a middle section of the balloon so that a distal end of the stent is disposed proximally of the distal end of the balloon and a proximal end of the stent is spaced distally from the proximal end of the balloon leaving a proximal section and a distal section of the balloon uncovered by the stent. The stent is then crimped onto the balloon to leave the stent with an initial outer diameter.

A dual section enclosure or retainer such as a stepped tube is provided which comprises a first section having a first inner diameter that is connected to a second section having a second inner diameter. The first inner diameter of the first section is greater than the second inner diameter of the second section. The second inner diameter is greater than the initial outer diameter of the stent but is a close approximation thereto. The enclosure is slid over the balloon catheter so that the larger first section of the enclosure is disposed over the proximal section of the balloon and the smaller second section of the enclosure is disposed over the stent and the distal section of the balloon. Then, the balloon is partially inflated so that the proximal section of the balloon inflates and engages the larger first section of the enclosure and the stent and distal section of the balloon are prevented from substantial expansion by the smaller second section of the enclosure. The partial inflation of the stent is typically performed at a lower pressure than the pressure used for inflation of the balloon in a vascular system. The enclosure is removed thereby leaving a proximal section of the balloon with a larger diameter than the stent to provide the benefits described above.

As an alternative, instead of a stepped tube or stepped enclosure as described above, a modified crimping assembly is provided which includes a plurality of crimping elements that form an iris-type opening for providing cylindrical crimping or radial compression of the stent. At least some of the crimping elements include a cut-out portion that is slightly enlarged to simulate the configuration of the stepped tube described above. Thus, the balloon and stent are placed in the crimping element with the stent in alignment with the non-cut-out portion of each crimping element and the proximal section of the balloon in alignment with the cut-out portions of the crimping elements. Then the stent may be crimped and, while the crimping device is in the crimping position, the balloon may be partially inflated to leave the proximal section of the balloon with a slightly larger diameter than the stent as described above. A heating element may also be easily incorporated into this device thereby enabling the stent and balloon to be heated before, during or after the crimping operation as well as the before, during or after the pressurization of the balloon.

Instead of a crimping device as discussed above with the crimping elements having cut-out portions, a crimping device can be provided with pairs of aligned crimping elements. Each pair could include a first crimping element designed to provide the larger first diameter for the proximal section of the balloon and a second crimping element designed to provide the second smaller diameter for the stent and distal section of the balloon as discussed above.

Although the above-identified figures disclose two embodiments, other variations thereof are also contemplated. It should be understood, that numerous modifications and other alternative embodiments may be devised by those skilled in the art which will fall within the spirit and scope of this disclosure and the appended claims.

DETAILED DESCRIPTION OF THE PRESENTLY PREFERRED EMBODIMENTS

Figure 1:
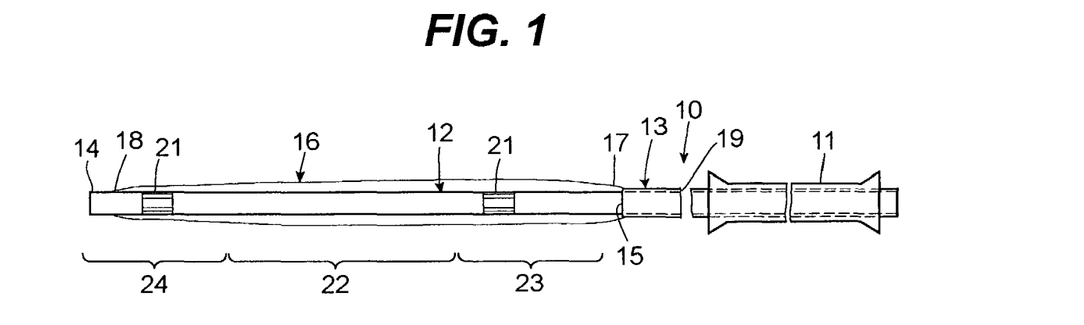
FIG. 1 is a sectional view of a distal end of a balloon catheter with a protective sleeve premounted thereon.

FIG. 1 illustrates a balloon catheter 10 with a protective sleeve 11 pre-loaded thereon. The balloon catheter 10 includes an inner tube 12 disposed within an outer tube 13. The inner tube 12 terminates at a distal end 14 and the outer tube 13 terminates at a distal end 15. The distal end 15 of the outer tube 13 is connected to a balloon 16 which, in turn, is also connected to the distal end 14 of the inner tube 12.

More specifically, the balloon 16 includes a proximal end 17 connected to the distal end 15 of the outer tube 13 and the balloon 16 further includes a distal end 18 connected to the distal end 14 of the inner tube 12. The annular gap shown at 19 between the outer tube 13 and inner tube 12 can be used for the communication of air or fluid to pressurize the balloon 16 as described below. The inner tube 12 may also be connected to one or more markers 21 for tracking the location of the balloon catheter 10 and, more specifically, the stent 25 (see FIG. 2), within a vascular system. For purposes of illustration below, the balloon 16 may also be considered to include a middle section shown at 22, a proximal section shown at 23 and a distal section shown at 24 in FIG. 1.

Figure 2:
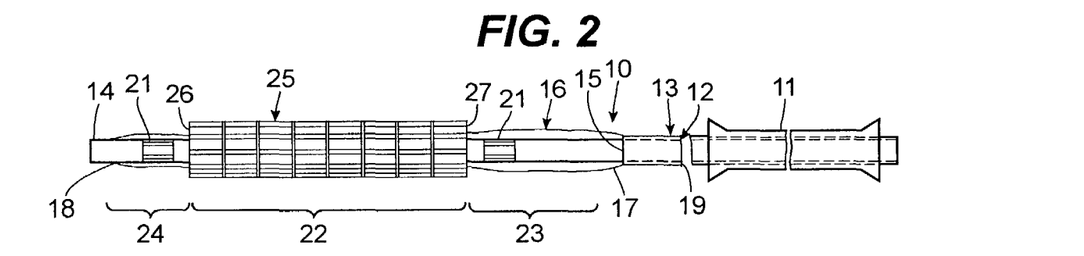
FIG. 2 is a sectional view of the distal end of the balloon catheter shown in FIG. 1 with an uncrimped tubular stent disposed over a distal portion of the balloon.

Turning to FIG. 2, a tubular stent 25 is mounted over the section or body 22 of the balloon 16. As shown in FIG. 2, the stent 25 is not yet crimped and includes a distal end 26 and a proximal end 27. The distal end 26 of the stent 25 is disposed proximally of the distal end 18 of the balloon 16 leaving, the distal section 24 of the balloon uncovered. The proximal section 23 of the balloon 16 also remains uncovered by the stent 25. The distal section 24 of the balloon 16 may be relatively short with the distal end 26 of the stent 25 closely aligned with the distal end 18 of the balloon 16 or the distal section 24 may be as long as the proximal section 23 of the balloon 16. Thus, the placement of the stent 25 on the balloon 16 may be symmetric or asymmetric.

Figure 3:
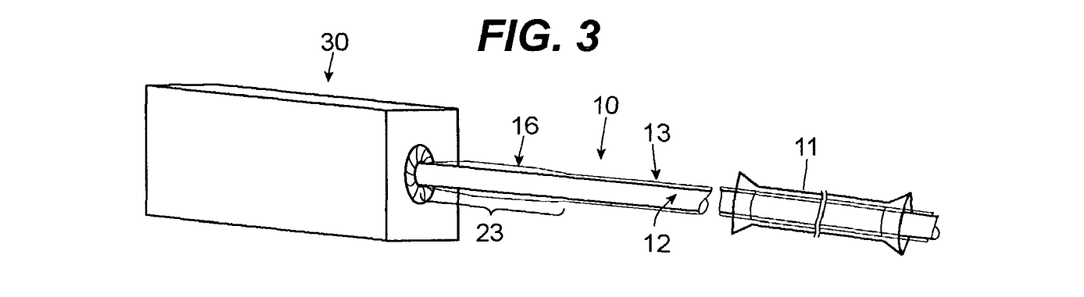
FIG. 3 illustrates, schematically, a device for crimping the stent onto the balloon.

Turning to FIG. 3, the stent 25 is crimped onto the middle section 22 of the balloon 16 using a conventional crimping device such as that shown in 30 in FIG. 3. Such a crimping tool 30 may be an automated machine or a hand-held crimping device. Conventional crimping methods may be employed in addition to the technique illustrated in FIGS. 10-13 below. The crimping procedure may be performed with or without heat. If heat is utilized, a typical crimping process will include the application of radial compression by way of the crimping tool 30 for a time period typically less than one minute and at a temperature ranging from about 50 to about 85° C. However, the crimping may be performed at any temperature that does not exceed the melting temperature of the balloon material.

Figure 4:
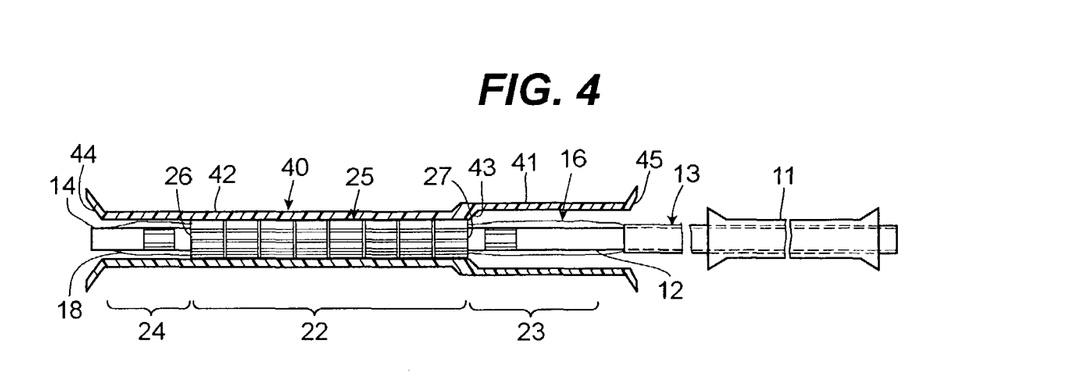
FIG. 4 is a sectional view of the distal end of the balloon catheter after the stent has been crimped onto the balloon and after a stepped tube has been placed over the distal end of the balloon catheter.

Turning to FIG. 4, after the stent 25 is crimped into place over the middle section 22 of the balloon 16, a stepped tube 40 or other dual diameter enclosure is slid over the distal end 14 of the balloon catheter 10 or inner tube 12. The stepped tube 40 includes a larger first section 41 and a smaller second section 42. The larger first section 41 has a diameter that is greater than that of the smaller second section 42. As shown in FIG. 4, the larger first section 41 is disposed over the proximal section 23 of the balloon 16 while the smaller second section 42 is disposed over the distal section 24 of the balloon 16 and the crimped stent 25, which is crimped onto the middle section 22 of the balloon 16. The smaller section 42 of the stepped tube 40 includes a proximal end 43 that is aligned with or slightly proximal to the proximal end 27 of the crimped stent 25. The distal end 44 of the smaller section 42 is either aligned with the distal end 18 of the balloon 16 and is disposed distally of the distal end 26 of the crimped stent 25 as shown in FIG. 4. Preferably, the proximal end 45 of the larger section 41 of the stepped tube 40, like the distal end 44 of the second section 42, is flared so as to avoid any damage to the crimped stent 25 during installation of the tube 40 over the balloon catheter 10 to the position shown in FIG. 4.

Figure 5:
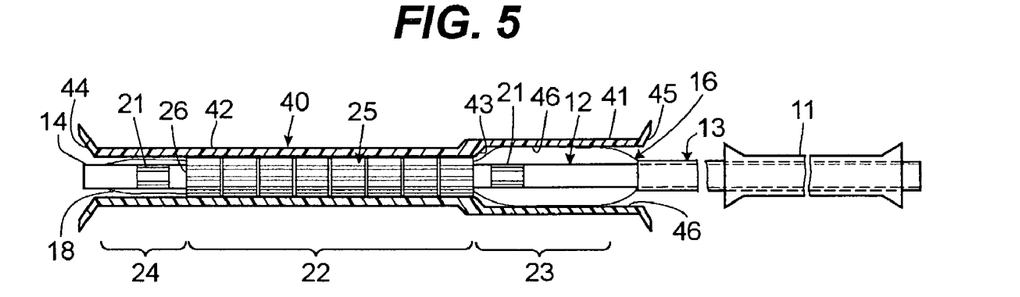
FIG. 5 is a sectional view of the distal end of the balloon catheter shown in FIG. 4 after internal pressure has been applied to the balloon to inflate a proximal section thereof.

Turning to FIG. 5, with the stepped tube 40 in the position shown in FIGS. 4 and 5, internal pressure to the balloon is communicated through the annular passage 19 to inflate the proximal section 23 (see FIG. 1) of the balloon 16 so that the proximal section 23 of the balloon 16 engages the internal surface 46 of the larger section 41 of the stepped tube 40. Expansion of the distal section 24 of the balloon 16 and the crimped stent 25 is prevented by the smaller section 42 of the stepped tube 40. In other words, the smaller section 42 of the stepped tube 40 has an internal diameter that closely matches that or is slightly larger than the outer diameter of the crimped stent 25 and the wrapped distal section 24 of the balloon 16. Thus, the smaller section of the step tube 42 prevents expansion of the crimped stent 25 and the distal section 24 of the balloon 16 as; shown in FIG. 5.

Figure 6:
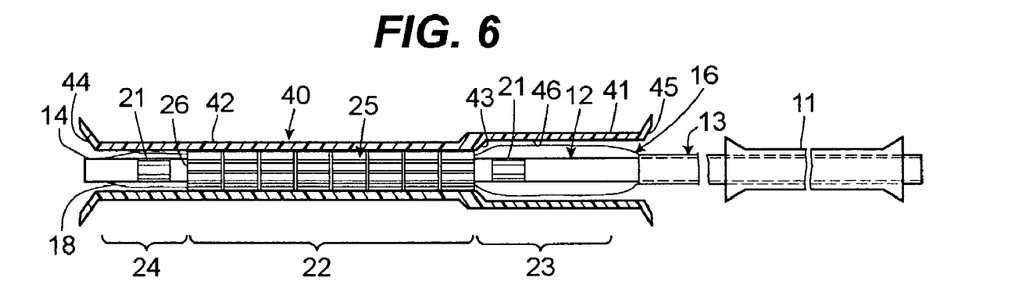
FIG. 6 is a sectional view of the balloon catheter of FIG. 5 after the internal pressure within the balloon has been released thereby leaving an enlarged proximal section of the balloon.

Meanwhile, the proximal section 23 of the balloon 16 is free to expand to the inner diameter of the larger first section 41 of the step tube and any further expansion of the proximal section 23 of the balloon 16 is prevented by engagement with the inner surface 46 of the first section 41 of the stepped tube 40. As shown in FIG. 6, upon release of internal pressure within the balloon 16, the proximal section 23 of the balloon 16 retracts to a slightly expanded or pillowed condition. The proximal section 23 of the balloon 16 no longer engages the inner wall 46 of the larger first section 41 of the stepped tube 40 but, as shown in FIG. 7, the proximal section 23 of the balloon 16 has an unexpanded outer diameter that slightly exceeds that of the crimped stent 25.

During inflation of the balloon 16 with the stepped tube 40 disposed thereon as shown in FIG. 5, heat may be applied to the distal portion of the catheter 10 and stent 25 to further secure the stent 25 to the middle section 22 of the balloon 16. If heat is utilized, heat can be applied by way of a hot air stream or other suitable heating medium and the pressurization of the balloon 16 can be carried out for a time period of less than or about a minute at an elevated temperature ranging from about 40° C. to about 85° C. or at an ambient temperature. The internal pressure of the balloon during the pressurization or inflation may range from about 30 psi to about 75 psi.

Figure 7:
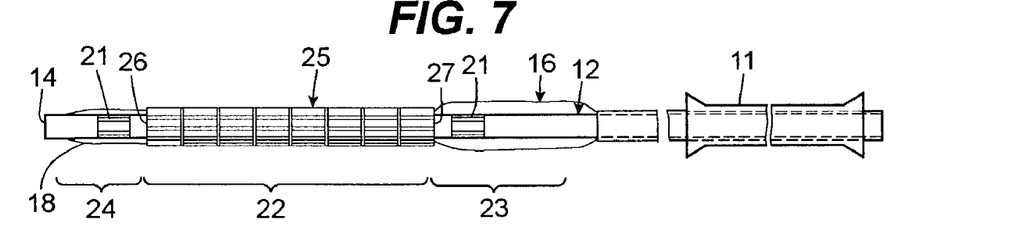
FIG. 7 is a sectional view of the balloon catheter of FIG. 6 after removal of the stepped tube.
Figure 8:
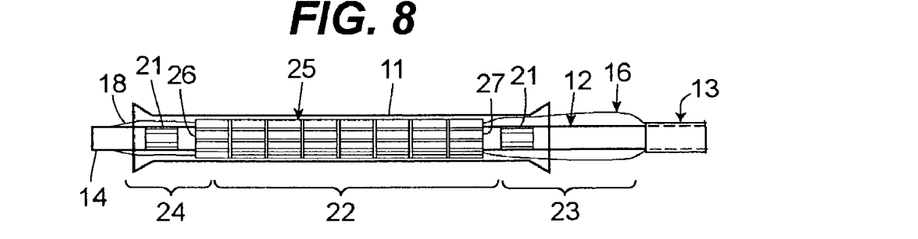
FIG. 8 is a sectional view of the balloon catheter of FIG. 7 after the protective sleeve has been moved over the stent.

The slightly larger outer diameter of the proximal section 23 of the balloon 16 shown in FIG. 7 provides two key advantages for the balloon catheter 10 as equipped with a crimped stent 25. First, the pillowing effect provided by the proximal section 23 of the balloon 16 protects the crimped stent 25 and more specifically, the proximal end 27 of the crimped stent 25 from being frictionally engaged by a vessel wall as the balloon catheter 10 is withdrawn or retracted in the proximal direction. Specifically, after inserting the balloon catheter 10, with the stent 25 crimped thereon, into a vascular system, the physician may decide, for a number of different reasons, to withdraw the entire apparatus 10 without deploying the stent 25. If this decision is made, and the balloon catheter 10 is withdrawn, it is imperative that the stent 25 remain in place over the proximal section 22 of the balloon 16. Frictional engagement of the stent 25, and most probably the proximal end 27 of the stent 25, against a vessel wall or vascular passage way, could result in dislodgment of the stent 25 from the balloon 16. Then, the stent 25 would need to be retrieved from the vascular system through a separate procedure thereby causing unnecessary trauma to the patient. Thus, to protect the stent 25 from dislodgment from the balloon 16 during a withdrawal or retractment procedure, a proximal section 23 of the balloon 16 is provided with a slightly larger diameter as shown in FIG. 7. The slightly larger diameter of the proximal section 23 of the balloon 16 is provided by the inflation process used with the stepped tube 40 as illustrated in FIGS. 4-6.

Thus, after the procedure illustrated in FIGS. 4-6 is completed, the stepped tube 40 is removed and the protective sleeve 11 is disposed over the stent 25 and the balloon catheter 10 is ready for packaging. The stepped tube 40 is further illustrated in FIG. 9, wherein the distal end 44 of the smaller first section 41 is flared as is the proximal end 45 of the larger second section 42. The flared end 45 protects the stent 25 as the stepped tube is slide over the stent 25 to the position shown in FIGS. 4-6. Also, as shown in FIGS. 4-6, the first and second sections 41, 42 may overlap one another. Further, it is preferable that the step tube 40 be fabricated from a clear plastic material so as to facilitate alignment of the proximal end 43 of the first section 41 with the proximal end 27 of the crimped stent 25 (see FIGS. 4-6).

Figure 9:
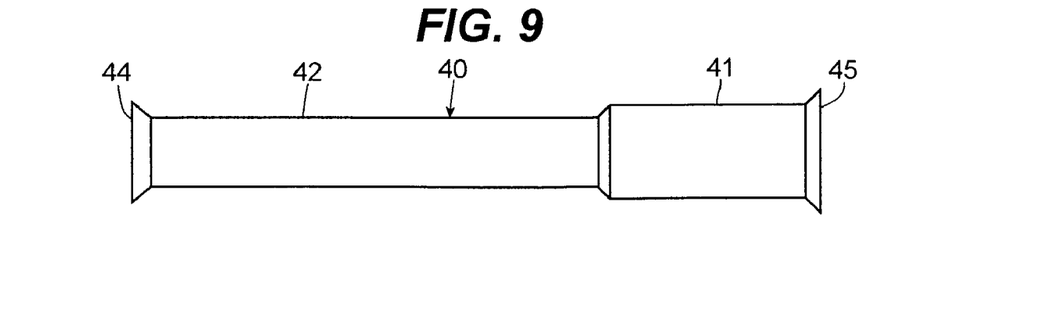
FIG. 9 is a plan view of the stepped tube shown in FIGS. 4-6.

It has been found that the suitable difference for the internal diameters of the first section 41 and second section 42 of the stepped tube 40 is about 0.02 in., however, other differences in the internal diameters of the sections 41, 42 of the tube 40 will also be suitable. Applicants have found the 0.02 in difference provides suitable stent protection for catheter systems having stent diameters ranging from 2.25 to 5.00 mm. However, it is anticipated that differences in the internal diameters between the first section 41 and second section 42 of the stepped tube 40 may vary widely depending upon stent size, balloon material, intended use, etc.

Figure 10:
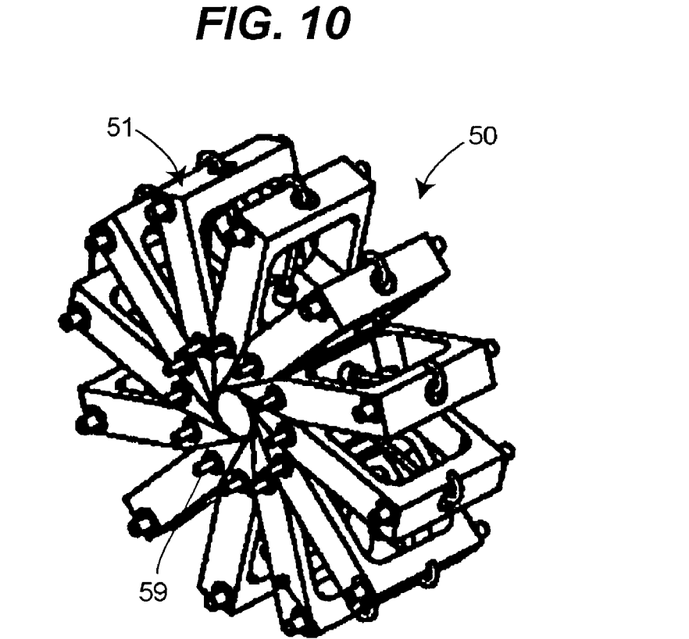
FIG. 10 is a partial view of a modified crimping device capable of providing the stepped configuration similar to that of the stepped tube shown in FIGS. 4-6 and 9.
Figures 11, 11A, 11B:
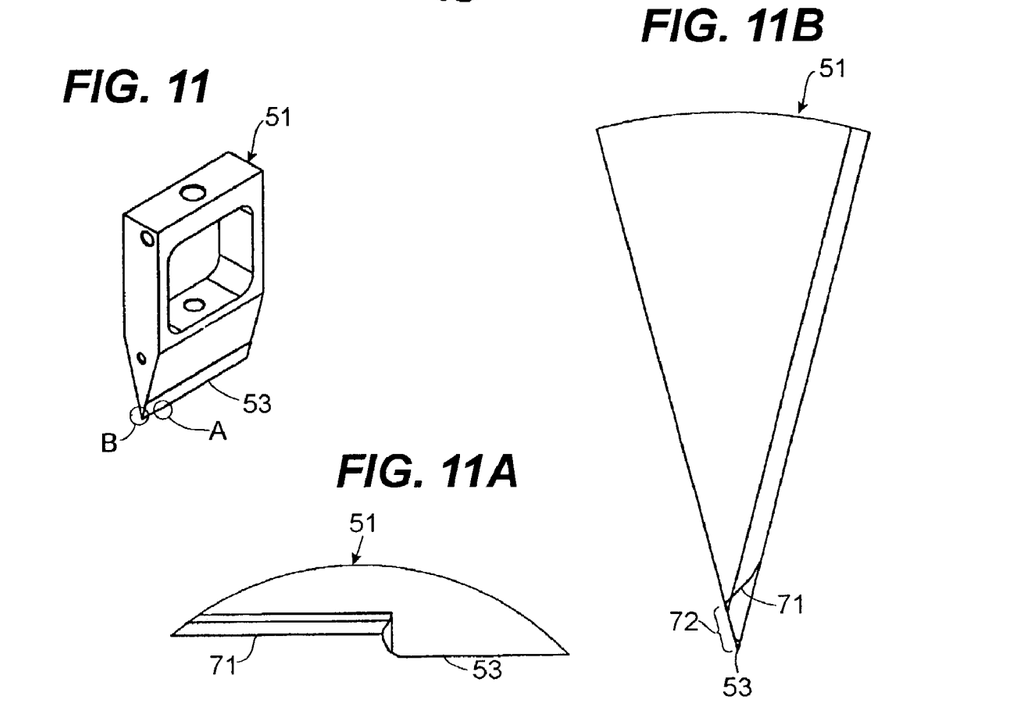
FIG. 11 is a perspective view of one of the crimping elements of the device illustrated in FIG. 10.
FIG. 11A is an enlarged detailed view of the area A of FIG. 11.
FIG. 11B is an enlarged detailed view of the area B of FIG. 11.
Figure 12:
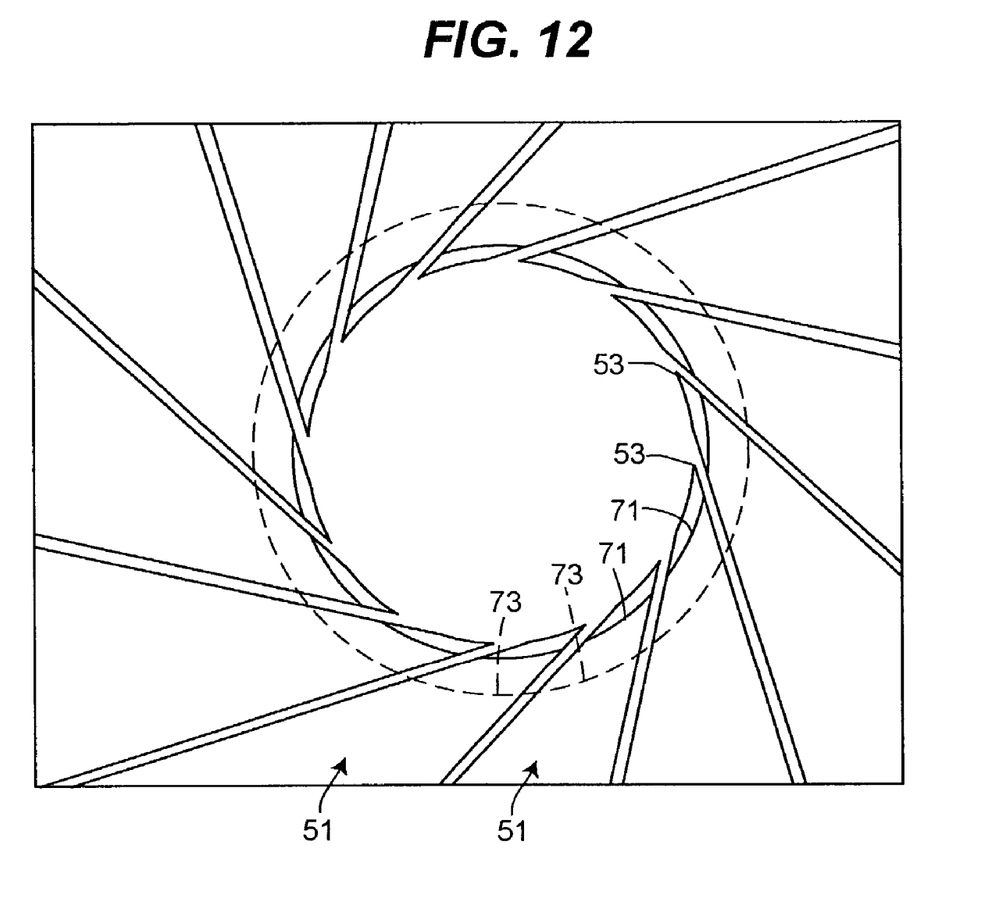
FIG. 12 is an end view of the crimping elements of the crimping device shown in FIGS. 10-11; particularly illustrating the stepped configuration of the crimping elements, one of which is shown in FIG. 11.

Instead of using a conventional crimping device 30 as shown in FIG. 3, a modified crimping device 50 as shown in FIGS. 10-12 may be employed which would eliminate the need for the stepped tube 40. The device shown at 50 in FIG. 10 is available from Machine Solutions, Inc. (www.machinesolutions.org). Another suitable device is disclosed in published U.S. patent application 2002-0138966 (Oct. 3, 2002). As shown in FIGS. 10-12, the crimping device 50 includes 12 tangentially arranged crimping elements 51, one of which is shown in detail in FIG. 11. The number of crimping elements 51 may vary. The crimping elements 51 are moved between a resting and crimping position by applying rotation movement to one or both of the actuating arms (not shown). Each element 51 includes a lower leading edge 53 shown in FIG. 11 which includes a stepped configuration as discussed with respect to FIGS. 11A and 11B below.

Turning to FIGS. 11, 11B and 11A, it will be noted that the leading edge 53 of each element 51 includes a cut-out portion 51 as illustrated by the detail A in FIG. 1A. An end view of the cut-out portion 71 is provided in the detail B of FIG. 11B. The cut-out 71 has an effective depth 72 from the leading edge 53. The leading edge 53 has a length that closely approximates that of the stent 25 to be crimped. In contrast, the length of the cut-out 71 closely approximates that of the proximal portion 23 of the balloon 16 which is to be partially inflated to provide protection to the proximal end 27 of the stent 25 as discussed above. Thus, instead of using the stepped tube 40, a crimping mechanism 50 is employed with a stepped configuration built-in to each crimping element 51.

FIG. 12 provides an end view of twelve such crimping elements 51, each with leading edges 53 and corresponding cut-out portions 71. The elements 51 are shown in the crimping position in FIG. 12 and are movable to a retracted position as shown by the phantom line 73. Another alternative would be to provide matched pairs of crimping elements that provide the larger and smaller crimping diameters desired.

The balloon 16 may be a single layer or multiple layer structure achieved through lamination processes or co-extrusion processes known to those skilled in the art. Suitable materials for the balloon include, but are not limited to nylon, PET, PEEK, PEBAX and mixtures thereof, co-extrusions thereof or laminations thereof. The relative length of the proximal section 43 should be less than the middle section 22 and the length of the distal section 24 should also be less than the middle or stent bearing section 24. Thus, the length ratios middle section 22: proximal section 23 and middle section 22: distal section 24 should both be greater than one (1) and the length ratio proximal section 23 distal section 24 should be greater than or equal to one (1).

The stent 25 design and materials may also vary widely. Suitable materials for the stent include, but are not limited to stainless steel, NITNOL, niobium, cobalt and alloys thereof.

Although specific embodiments and methods have been described, workers skilled in the art will realize that changes may be made in form and detail without departing from the spirit and scope of this disclosure.

What is claimed is:

1. A method for fabricating a balloon catheter stent deployment system, the method comprising:
    providing a balloon catheter comprising
        an inner tubular shaft disposed within an outer tubular shaft, the inner and outer shafts each having proximal and distal ends, the distal end of the inner shaft extending distally beyond the distal end of the outer shaft, and
        an inflatable balloon having a proximal end attached to the outer shaft near the distal end thereof and a distal end attached to the inner shaft near the distal end thereof;
    placing a stent over the balloon so that a distal end of the stent is disposed proximally to the distal end of the balloon leaving a distal section of the balloon extending from the distal end of the stent to the distal end of the balloon uncovered by the stent,
    crimping the stent onto the balloon to leave the stent with an initial outer diameter,
    placing a stepped enclosure over the stent and balloon wherein the stepped enclosure comprising a first section having a first inner diameter and that is connected to a second section having a second inner diameter, the first inner diameter being greater than the second inner diameter, the second inner diameter being greater than the initial outer diameter of the stent but in close approximation thereto, the second section of the stepped enclosure being longer than the stent, and wherein the first section of the stepped enclosure is disposed over a proximal section of the balloon and the second section of the stepped enclosure is disposed over the stent and the distal section of the balloon uncovered by the stent,
    inflating the balloon so that the proximal section of the balloon inflates and engages the first section of the stepped enclosure and the stent and a portion of the balloon disposed beneath the stent and the distal section of the balloon uncovered by the stent are prevented from substantial expansion by the second section of the stepped enclosure, and the maximum outer diameter of the distal section of the balloon uncovered by the stent is no greater than the initial outer diameter of the stent,
    removing the balloon and stent from the stepped enclosure.

2. The method of claim 1 further comprising:
    inserting a protective sleeve over the stent after removing the balloon and stent from the stepped enclosure.

3. The method of claim 1 further comprising:
    inserting a protective sleeve over the balloon catheter to a position proximal to the stent and balloon before placing the stent over the balloon, and sliding the protective sleeve over the stent after removing the stepped tube.

4. The method of claim 1 wherein the first section of the stepped enclosure comprises a flared proximal end and the second section of the stepped enclosure comprises a flared distal end.

5. The method of claim 1 wherein the stepped enclosure is a stepped tube and the second section of the stepped tube extends into the first section of the stepped tube to provide an overlap section between the first and second sections.

6. The method of claim 1 wherein the stepped enclosure is formed by a plurality of crimping elements each having a stepped leading edge to form the stepped enclosure and wherein the plurality of crimping elements are movable between crimping and retracted positions.

7. The method of claim 6 wherein the plurality of crimping elements comprise part of a crimping device capable of heating the stent and balloon during the crimping of the stent onto the balloon.

8. The method of claim 1 wherein the crimping further comprises heating the stent and balloon to a temperature ranging from about 50 to about 85° C.

9. The method of claim 1 wherein the crimping further comprises heating the stent and balloon to a temperature of about 65° C.

10. The method of claim 1 wherein the inflating further comprises inflating the balloon with a gas having a temperature ranging from about 40 to about 60° C.

11. The method of claim 1 wherein the inflating further comprises pressurizing the balloon to an internal pressure ranging from about 30 to about 75 psi for a time period ranging from about 5 seconds to about 1 minute.

12. The method of claim 1 wherein the inflating further comprises inflating the balloon with a gas having a temperature ranging from about 40 to about 60° C. and pressurizing the balloon to an internal pressure ranging from about 30 to about 75 psi for a time period ranging from about 5 seconds to about 1 minute.

* * * * *